United States Patent [19]

Stanley et al.

[11] 3,951,996

[45] Apr. 20, 1976

[54] PROCESS FOR MAKING NICOTINIC ACID HYDRAZIDES

[75] Inventors: Robert Holroyd Stanley, Durham; Barry Leigh Shaw, Teesside, both of England

[73] Assignee: British Titan Limited, Billingham, Teesside, England

[22] Filed: Dec. 12, 1973

[21] Appl. No.: 426,669

[30] Foreign Application Priority Data

Jan. 4, 1973  United Kingdom.................. 513/73

[52] U.S. Cl. ..................... 260/295 H; 260/295 AM; 260/295.5 H; 260/295.5 A; 260/558 H; 260/558 P; 260/561 H; 260/561 R; 260/562 H; 260/562 R

[51] Int. Cl.² ........................................ C07D 213/56

[58] Field of Search ............ 260/295.5 A, 295 AM, 260/558 R, 295 H, 561 R, 562 H, 295.5 H, 557 H, 558 H, 561 H

[56] References Cited
UNITED STATES PATENTS

| | | |
|---|---|---|
| 3,026,324 | 3/1962 | Mueller et al. .............. 260/295.5 A |
| 3,072,726 | 1/1963 | Gutmann et al................ 260/557 H |
| 3,801,610 | 4/1974 | Werdehausen et al. ........ 260/561 R |
| 3,816,483 | 6/1974 | Werdehausen et al. ........ 260/561 R |
| 3,822,277 | 7/1974 | Dufour......................... 260/295.5 A |

OTHER PUBLICATIONS

Millar et al. "A Shorter Sidgwick's Organic Chemistry of Nitrogen" (1969) p. 384.

Primary Examiner—Henry R. Jiles
Assistant Examiner—Robert W. Ramsier
Attorney, Agent, or Firm—Schuyler, Birch, Swindler, McKie & Beckett

[57] ABSTRACT

A process for condensing a carboxylic acid with ammonia, hydrazine or a substituted hydrazine or a primary or secondary amine to give a compound containing the group —CO—NR'— where R' is a hydrogen atom, an organic radical, an $NH_2$ group or a substituted $NH_2$ group by the use of a catalyst having a formula $M(OR)_nX_{(4-n)}$ wherein M represents titanium or zirconium, R represents an alkyl or aryl radical, X represents a halogen atom and n is an integer from 1 to 4.

10 Claims, No Drawings

PROCESS FOR MAKING NICOTINIC ACID HYDRAZIDES

The present invention relates to an improved process in which a carboxylic acid is condensed with a nitrogen-containing compound of the type hereinafter specified.

Accordingly, the present invention comprises condensing a carboxylic acid with ammonia, hydrazine or a substituted hydrazine or a primary or secondary amine in the presence of a catalyst having the formula $M(OR)_nX_{(4-n)}$ wherein M represents titanium or zirconium, R represents an alkyl or aryl radical, X represents a halogen atom and $n$ is an integer from 1 to 4 inclusive and thereafter recovering a compound containing the group —CO—NR'— where R' is a hydrogen atom, an organic radical, an $NH_2$ group or a substituted $NH_2$ group.

The carboxylic acid may be a compound containing one or more carboxylic acid groups, for example a nicotinic acid such as iso-nicotinic acid (which may conveniently be reacted with hydrazine to produce the iso-nicotinic acid hydrazide, otherwise known commercially as "Isonazid"). Other examples of carboxylic acids are amino acids which may conveniently be reacted together by the process of the present invention to produce long chain compounds containing a number of —CO—NH— linkages, i.e. peptides or proteins. Alternatively, the reaction may be used to form ring compounds by the condensation of a carboxylic acid group and a primary or secondary amine group on the same molecule (providing the groups are separated by a suitable number of carbon or other atoms to form the desired homogeneous or heterogeneous ring compound). The synthesis of barbiturate compounds is also envisaged by the present process since these normally contain the group —CO—NR'—.

The foregoing list of reactions is not, of course, intended to be exhaustive and many other suitable reactions will occur to a skilled worker in the field.

As noted, the reaction is between a carboxylic acid and ammonia, hydrazine or a substituted hydrazine or a primary or secondary amine. Tertiary amines are, of course, unsuitable since they do not possess a hydrogen atom on the nitrogen which will condense with the carboxylic acid group.

It is preferred that the reaction be carried out in a homogeneous reaction mixture and in this case the reactants and catalyst will normally be dissolved in a solvent. The solvent is preferably a polar solvent, for example an alcohol and conveniently a lower alcohol such as a butyl or an aryl alcohol. During the reaction the water formed is removed and this may conveniently be accomplished by continuous distillation to remove the water as an azeotropic mixture from the reactant solvent, for example with added toluene.

Although the reactants are preferably dissolved in a solvent, as noted above, the reaction product, i.e. the compound containing the —CO—NR'— group, may be, and preferably is, insoluble in the reaction mixture and precipitates out as the reaction continues.

The preferred catalyst is an alkoxide (or polymer thereof) wherein M is titanium, or zirconium, the R group is an alkyl group containing from 1 to 4 carbon atoms and the integer $n$ is 4. Compounds where R is a methyl, ethyl, propyl or butyl radical are particularly preferred.

Catalysts containing titanium are generally more active than the corresponding catalysts containing zirconium. Where contamination with titanium occurs this can be readily removed by dissolving the product in a solvent in which the titanium is insoluble, filtering, removing the remaining solvent and thereafter recrystallising the product. If desired a second recrystallisation can be carried out. In the case of iso-nicotinic acid hydrazide (or "Isonazid") the recrystallisation may conveniently be carried out using 95% ethyl alcohol.

Amounts of the catalyst in the range 0.1% to 10% w/w on the reaction mixture are conveniently used and amounts in the range 2% to 4% are preferred.

The following Examples show processes according to the present invention:

EXAMPLE 1

Iso-nicotinic acid, 0.48 g. mole, was added to a mixture of 0.516 g. mole of hydrazine hydrate and 65 ml. of n-butanol and the mixture was heated to form a clear solution. Toluene, 35 ml., was then added and the mixture heated to remove the water present in the hydrazine hydrate. The quantity of water removed was measured using a Dean and Stark apparatus and was found to be 10 ml.

Tetra-n-butoxy titanium, 3.0 g., or 9 m. mole was added to the mixture as a catalyst and the reaction mixture was heated until no more water was formed.

The compound which precipitated out weighed 52 g. and, after recrystallisation from 95% ethanol, had a melting point of 172°C, and an elemental analysis and infra-red spectrum indistinguishable from that of isonicotinic acid hydrazide. The yield of the pure material was in excess of 80%.

EXAMPLE 2

The process described above was repeated using tetra-n-butoxy zirconium 3.0 g., or 7.8 m. mole in place of the corresponding titanium compound.

Again, the product 57.5 g., was recrystallised from 95% ethanol and had a melting point of 172°C and an elemental analysis and infra-red spectrum indistinguishable from that of isonicotinic acid hydrazide. The yield of pure material was 86%.

EXAMPLE 3

Benzoic acid (0.5 mole) was added to a mixture of hydrazine hydrate (0.5 mole) and n-butyl alcohol (65 ml).

The mixture was heated to form a clear solution and toluene (35 ml) was added. The water present due to the hydrazine hydrate was removed by azeotropic distillation.

Tetra-n-butoxy titanium was then added (3.0 gm) to the mixture as a catalyst and the reaction mixture heated until no further water was removed.

Benzoyle hydrazide was recovered in 80% yield and identified by m.pt. 112° and by its infra-red spectrum.

EXAMPLE 4

The process was carried out as in Example 3 but substituting 0.5 mole of acetic acid for 0.5 mole of benzoic acid.

Acetic acid hydrazide was recovered in 95% yield identified by m.pt. 67° and by its infra-red spectrum.

EXAMPLE 5

A reaction mixture of aniline (0.5 mole), glacial acetic acid (0.5 mole), toluene (50 ml) and tetra n-butoxy titanium (3.0 g.) was heated until all the water formed during the reaction had been azeotropically removed.

Acetanilide was recovered in a yield 80%, identified both by m.pt and by its infra-red spectrum.

EXAMPLE 6

A process was carried out as in Example 5 but substituting benzoic acid for acetic acid.

Benzanilide was recovered in 99% yield, identified both by m.pt and by its infra-red spectrum.

EXAMPLE 7

A process was carried out as in Example 4 but substituting phenylhydrazine for hydrazine hydrate.

Acetyl-β-phenyl hydrazine was recovered in good yield and was identified by m.pt. and by its infra-red spectrum.

EXAMPLE 8

A process as described in Example 3 was carried out but substituting phenylhydrazine for hydrazine hydrate.

1-benzoyl-2-phenyhydrazine was recovered and identified by its m.pt. and infra-red spectrum.

EXAMPLE 9

Nicotinic acid (0.5 mole), diethylamine (0.5 mole), toluene (35 ml), n-butanol (60 ml) and tetra n-butoxy titanium were heated until all water was removed by azeotropic distillation from the reaction mixture. The volatile solvents were then distilled off and the remaining product fractionally distilled under vacuum to give nikethamide identified both by its boiling point and its infra-red spectrum.

EXAMPLE 10

A process as described in Example 9 was carried out substituting acetic acid for nicotinic acid. N,N-diethylacetamide was recovered in high yield from the reaction mixture, and was identified by its boiling point and its infra-red spectrum.

EXAMPLE 11

A process was carried out as described in Example 1 except that titanium tetrachloride replaced the tetra n-butoxy titanium. The product, was recovered in only 60% yield.

What is claimed is:

1. A process for producing a nicotinic acid hydrazide comprising condensing a nicotinic carboxylic acid with a compound selected from the group consisting of hydrazine and substituted hydrazine in the presence of a catalyst having the formula $M(OR)_n$ wherein M represents titanium or zirconium, R represents an alkyl radical having 1 to 4 carbon atoms, and $n$ represents an integer from 1 to 4 inclusive and thereafter recovering the nicotinic acid hydrazide.

2. A process as claimed in claim 1 wherein the nicotinic acid is iso-nicotinic acid which is condensed with hydrazine to form iso-nicotinic acid hydrazide.

3. A process as claimed in claim 1 wherein the reactants and catalyst are dissolved in a solvent.

4. A process as claimed in claim 3 wherein the solvent is an alcohol.

5. A process as claimed in claim 4 wherein the solvent is a butyl or an aryl alcohol.

6. A process as claimed in claim 1 wherein water is removed during the reaction by azeotropic distillation.

7. A process as claimed in claim 6 wherein toluene is added to the reaction mixture prior to or during distillation.

8. A process as claimed in claim 1 wherein the R group of the catalyst is an alkyl group containing 4 carbon atoms and $n$ is 4.

9. A process as claimed in claim 1 wherein the amount of catalyst present in the reaction mixture is in the range 0.1% to 10%, weight/weight.

10. A process as claimed in claim 9 wherein the amount of catalyst is in the range 2% to 4% weight/weight.

* * * * *